United States Patent
Kobayashi

(10) Patent No.: US 10,779,715 B2
(45) Date of Patent: Sep. 22, 2020

(54) ENDOSCOPE APPARATUS

(71) Applicant: Sony Olympus Medical Solutions Inc., Tokyo (JP)

(72) Inventor: Motoaki Kobayashi, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 24 days.

(21) Appl. No.: 15/893,784

(22) Filed: Feb. 12, 2018

(65) Prior Publication Data

US 2018/0235451 A1     Aug. 23, 2018

(30) Foreign Application Priority Data

Feb. 23, 2017  (JP) .................... 2017-032590
Dec. 4, 2017   (JP) .................... 2017-232882

(51) Int. Cl.
| A61B 1/05 | (2006.01) |
| G06T 5/00 | (2006.01) |
| A61B 1/00 | (2006.01) |

(52) U.S. Cl.
CPC .......... *A61B 1/05* (2013.01); *A61B 1/00186* (2013.01); *A61B 1/00188* (2013.01); *G06T 5/003* (2013.01); *G06T 2207/10068* (2013.01); *G06T 2207/20192* (2013.01)

(58) Field of Classification Search
CPC ... A61B 1/00186; A61B 1/00188; A61B 1/05; G06T 2207/10068; G06T 2207/20192; G06T 5/003

See application file for complete search history.

(56) References Cited

U.S. PATENT DOCUMENTS

| 4,157,216 | A | * | 6/1979 | Plummer | ............... | G03B 15/14 |
| | | | | | | 396/17 |
| 4,576,144 | A | * | 3/1986 | Ishii | .................. | A61B 1/00124 |
| | | | | | | 439/628 |
| 5,178,130 | A | * | 1/1993 | Kaiya | .................. | A61B 1/0005 |
| | | | | | | 348/68 |
| 5,270,825 | A | * | 12/1993 | Takasugi | ............... | A61B 1/042 |
| | | | | | | 348/335 |

(Continued)

FOREIGN PATENT DOCUMENTS

JP    2012-109826    6/2012

*Primary Examiner* — Peter D Le
(74) *Attorney, Agent, or Firm* — Xsensus LLP

(57) ABSTRACT

An endoscope apparatus includes: a first endoscope that includes a first observation optical system; a second endoscope that includes a second observation optical system different from the first observation optical system, an exit pupil diameter of the second endoscope being larger than an exit pupil diameter of the first endoscope; an imaging device that is connected to one of the first and the second endoscopes, and includes an aperture diaphragm configured to pass light output from the connected one of the first and the second endoscopes, and an imaging unit configured to receive the light passed through the aperture diaphragm and convert the received light into an electric signal; and an image processing device configured to generate an image by using the electric signal generated by the imaging device. A minimum aperture diameter of the aperture diaphragm is larger than the exit pupil diameter of the first endoscope.

7 Claims, 4 Drawing Sheets

(56) References Cited

U.S. PATENT DOCUMENTS

| | | | | |
|---|---|---|---|---|
| 5,315,383 | A * | 5/1994 | Yabe | A61B 1/042 348/68 |
| 5,392,067 | A * | 2/1995 | Konno | H04N 5/357 348/65 |
| 5,588,948 | A * | 12/1996 | Takahashi | A61B 1/00179 600/111 |
| 5,713,364 | A * | 2/1998 | DeBaryshe | A61B 1/00059 250/461.2 |
| 5,867,308 | A * | 2/1999 | Pensel | A61B 3/0025 359/368 |
| 5,876,327 | A * | 3/1999 | Tsuyuki | A61B 1/00096 600/112 |
| 5,929,901 | A * | 7/1999 | Adair | A61B 1/00135 257/E25.032 |
| 6,069,651 | A * | 5/2000 | Tsuyuki | G02B 23/2423 348/75 |
| 6,241,656 | B1 * | 6/2001 | Suga | A61B 1/05 600/109 |
| 6,461,346 | B1 * | 10/2002 | Buelna | A61M 25/10 604/104 |
| 6,540,668 | B1 * | 4/2003 | Schulz | A61B 1/055 600/112 |
| 2001/0012053 | A1 * | 8/2001 | Nakamura | A61B 1/00193 348/45 |
| 2002/0101507 | A1 * | 8/2002 | Saito | A61B 1/00022 348/65 |
| 2003/0122926 | A1 * | 7/2003 | Kumei | H04N 5/2254 348/65 |
| 2003/0139650 | A1 * | 7/2003 | Homma | A61B 1/0638 600/181 |
| 2003/0181823 | A1 * | 9/2003 | Gatto | A61B 1/00135 600/564 |
| 2004/0077928 | A1 * | 4/2004 | Moriyama | A61B 1/00089 600/127 |
| 2004/0080613 | A1 * | 4/2004 | Moriyama | A61B 1/00071 348/65 |
| 2005/0200842 | A1 * | 9/2005 | Bonningue | G02B 23/2469 356/241.1 |
| 2006/0025691 | A1 * | 2/2006 | Tanaka | A61B 8/12 600/459 |
| 2006/0224041 | A1 * | 10/2006 | Okada | A61B 1/012 600/106 |
| 2006/0264707 | A1 * | 11/2006 | Kinney | A61B 1/00151 600/115 |
| 2007/0049803 | A1 * | 3/2007 | Moriyama | A61B 1/00096 600/176 |
| 2007/0100202 | A1 * | 5/2007 | Murata | A61B 1/00059 600/109 |
| 2009/0312775 | A1 * | 12/2009 | Gilkey | A61B 1/018 606/147 |
| 2012/0053421 | A1 * | 3/2012 | Yoshida | A61B 1/07 600/182 |
| 2012/0215068 | A1 * | 8/2012 | Furuta | A61B 1/0008 600/125 |
| 2013/0182169 | A1 * | 7/2013 | Kosugi | G02B 23/2415 348/335 |
| 2014/0039259 | A1 * | 2/2014 | Okaniwa | A61B 1/005 600/139 |
| 2014/0275787 | A1 * | 9/2014 | Miyamoto | A61B 1/005 600/139 |
| 2015/0031952 | A1 * | 1/2015 | Long | A61B 1/00154 600/114 |
| 2015/0309284 | A1 * | 10/2015 | Kagawa | G02B 23/2453 348/76 |
| 2019/0029508 | A1 * | 1/2019 | Tabata | A61B 1/00096 |

\* cited by examiner

ENDOSCOPE APPARATUS

CROSS-REFERENCE TO RELATED APPLICATION(S)

The present application claims priority to and incorporates by reference the entire contents of Japanese Patent Application No. 2017-32590 filed in Japan on Feb. 23, 2017 and Japanese Patent Application No. 2017-232882 filed in Japan on Dec. 4, 2017.

BACKGROUND

The present disclosure relates to an endoscope apparatus.

For endoscope apparatuses configured to capture an image of an imaged object by using an imaging element and to observe the imaged object, there has been a demand for enhancing the resolution of the captured image for the purpose of obtaining a more precise observation image. For example, a known endoscope apparatus includes: an endoscope that is inserted in the body of a subject and takes in light from an imaged object; an imaging device including an imaging element that receives the light taken in by the endoscope and converts the received light into an electric signal; and an image processing device that generates a captured image on the basis of the electric signal generated by the imaging device.

As a technique for enhancing the resolution, imaging elements are developed so as to have a larger number of pixels. In that situation, when the aperture value becomes smaller due to the larger number of pixels, the depth of field is also decreased. As a result, a problem arises where, although the resolution of the captured image becomes higher, the depth of field is decreased, which may make it difficult to observe the imaged object in some situations depending on the imaged object.

As a technique for increasing the depth of field, a method is known by which the depth of field is increased by decreasing the diameter of the aperture of an aperture diaphragm. According to this method, it is possible to adjust the depth of field by adjusting the diameter of the aperture of the aperture diaphragm. However, when the depth of field is increased by applying the aperture diaphragm of an imaging device to a so-called thin endoscope having a small exit pupil diameter which is equal to the dimension of the image of an imaged object formed by an observation optical system included in the endoscope, there is a possibility that the optical axis of the observation optical system in the endoscope and the center of the aperture of the aperture diaphragm of the imaging device may become out of alignment, due to wobbling or the like occurring at the time of attaching the endoscope and the imaging device to each other. In that situation, there is a possibility that it may be impossible for the aperture diaphragm to properly narrow the aperture for the image of the imaged object and to properly increase the depth of field.

As another technique for increasing the depth of field, another method is disclosed (see Japanese Patent Application Laid-open No. 2012-109826, for example) by which, a phase modulation element is disposed at the incident pupil position of an observation optical system so that, when an image is generated on the basis of light that has passed through the phase modulation element, the depth of field is increased by generating the image while using a point spread function (PSF). This technique is generally called wavefront coding.

Further, as yet another technique for increasing the depth of field, another method is also possible by which, for example, a so-called contour enhancement process (an image processing process to enhance a contour) is applied to at least such a region where the captured image is out of focus so as to increase the depth of field by expanding the region having a clear contour.

SUMMARY

Incidentally, to the imaging device described above, it is possible to attach any one of different types of endoscopes having mutually-different optical characteristics. For example, an endoscope having the aforementioned phase modulation element and an endoscope having no phase modulation element may be attached. When it is possible to attach any of a plurality of types of endoscopes to an imaging device in this manner, it is necessary to be able to generate an image having an increased depth of field regardless of what type of endoscope is connected to the imaging device.

According to one aspect of the present disclosure, there is provided an endoscope apparatus including: a first endoscope that includes a first observation optical system; a second endoscope that includes a second observation optical system different from the first observation optical system, an exit pupil diameter of the second endoscope being larger than an exit pupil diameter of the first endoscope; an imaging device that is connected to one of the first and the second endoscopes, and includes an aperture diaphragm configured to pass light output from the connected one of the first and the second endoscopes, and an imaging unit configured to receive the light passed through the aperture diaphragm and convert the received light into an electric signal; and an image processing device configured to generate an image by using the electric signal generated by the imaging device, wherein a minimum aperture diameter of the aperture diaphragm is larger than the exit pupil diameter of the first endoscope.

According to another aspect of the present disclosure, there is provided an endoscope apparatus including: a first endoscope including a first observation optical system with a phase modulation element; a second endoscope including a second observation optical system without a phase modulation element, the second observation optical system being different from the first observation optical system; an imaging device that is connected to one of the first and the second endoscopes, and configured to receive light output from the connected one of the first and the second endoscopes, and convert the received light into an electric signal; and an image processing device that generates an image by using the electric signal generated by the imaging device, wherein when the first endoscope is connected to the imaging device, the image processing device generates the image by performing an image processing process that uses a point spread function, and when the second endoscope is connected to the imaging device, the image processing device generates the image by making a degree of enhancement in a contour enhancement process higher than that used when the first endoscope is connected to the imaging device.

DETAILED DESCRIPTION

Figure 1:
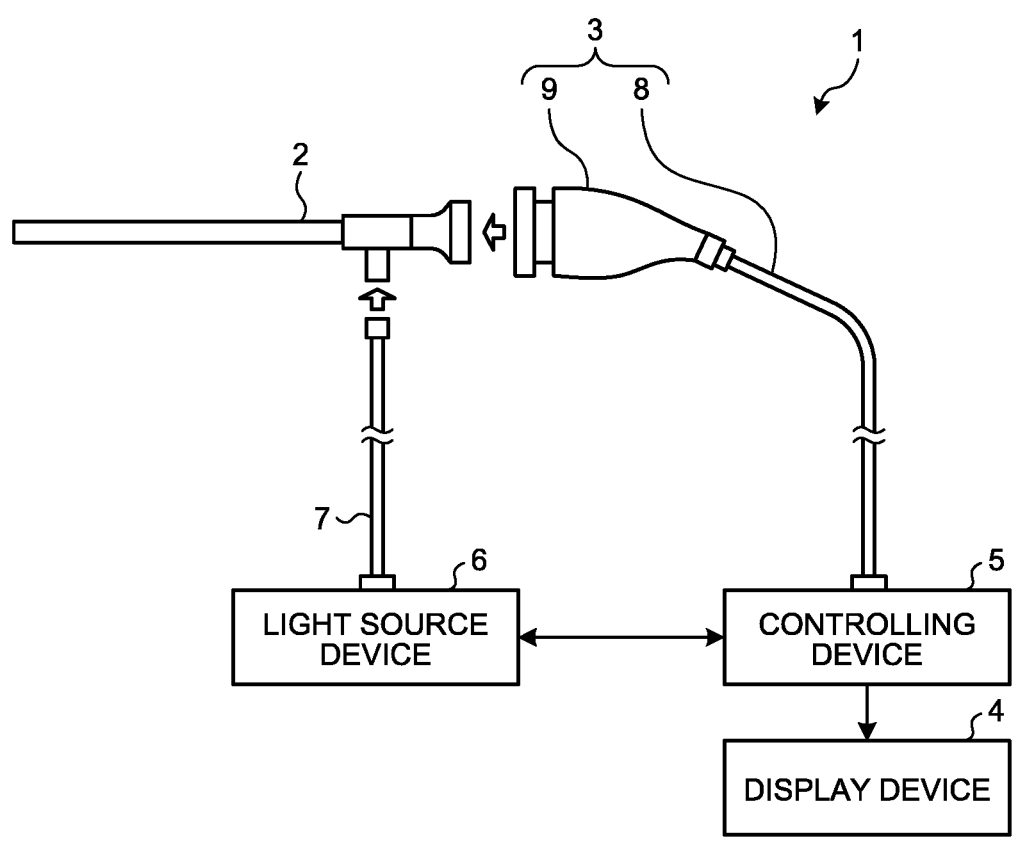
FIG. 1 is a drawing illustrating a schematic configuration of an endoscope apparatus according to an embodiment.

Embodiments will be explained below. In the embodiments, as an example of an endoscope apparatus, a medical endoscope apparatus that captures and displays an image of the inside of a subject such as a patient will be explained. Further, the present disclosure is not limited to the embodiments described below. Furthermore, in the description of the drawings, the same elements will be referred to by using the same reference characters.

Embodiments

FIG. 1 is a drawing illustrating a schematic configuration of an endoscope apparatus 1 according to an embodiment. The endoscope apparatus 1 is an apparatus used in the medical field and is used for observing an imaged object on the inside of an observed subject (the inside of a living body) such as a human being. As illustrated in FIG. 1, the endoscope apparatus 1 includes an endoscope 2, an imaging device 3 (a medical imaging device), a display device 4, a controlling device 5 (an image processing device), and a light source device 6. The imaging device 3 and the controlling device 5 structure a medical image obtaining system. In a first embodiment, the endoscope 2, the imaging device 3, and the controlling device 5 structure the endoscope apparatus using the endoscope configured with a rigid endoscope, for example.

The light source device 6 has one end of a light guide 7 connected thereto and is configured to supply illumination light (e.g., white light) used for illuminating the inside of the living body to the one end of the light guide 7. The one end of the light guide 7 is detachably connected to the light source device 6, whereas the other end of the light guide 7 is detachably connected to the endoscope 2. Further, the light guide 7 is configured to transfer the light supplied thereto by the light source device 6 from the one end to the other end, so as to supply the light to the endoscope 2.

The imaging device 3 is configured to capture an image of the imaged object provided from the endoscope 2 and to output the imaged result. As illustrated in FIG. 1, the imaging device 3 includes a transfer cable 8 serving as a signal transfer unit and a camera head 9. In the first embodiment, the transfer cable 8 and the camera head 9 structure the medical imaging device.

The endoscope 2 is rigid, has an oblong shape, and may be inserted into the inside of the living body. Provided on the inside of the endoscope 2 is an observation optical system that is structured by using one or more lenses and is configured to condense the image of the imaged object. The endoscope 2 is configured to emit the light supplied thereto via the light guide 7 from the distal end thereof, so as to radiate the light onto the inside of the living body. Further, the light radiated onto the inside of the living body (the image of the imaged object) is condensed by the observation optical system (a lens unit 92) provided in the endoscope 2.

The camera head 9 is detachably connected to the proximal end of the endoscope 2. Further, under control of the controlling device 5, the camera head 9 is configured to capture the image of the imaged object condensed by the endoscope 2 and to output a captured image signal obtained by the imaging process. Detailed configurations of the camera head 9 will be explained later.

One end of the transfer cable 8 is detachably connected to the controlling device 5 via a connector, whereas the other end of the transfer cable 8 is detachably connected to the camera head 9 via a connector. More specifically, the transfer cable 8 is a cable in which a plurality of electric wires (not illustrated) are provided on the inside of an outer coating forming the outermost layer. The plurality of electric wires are electric wires used for transferring the captured image signal output from the camera head 9 to the controlling device 5 and transferring a control signal, a synchronization signal, a clock signal, and electric power output from the controlling device 5 to the camera head 9.

Under control of the controlling device 5, the display device 4 is configured to display an image generated by the controlling device 5. To make it easier to achieve a sense of immersion during observation processes, it is desirable to configure the display device 4 to have a display unit of 55 inches or larger; however, possible specifications are not limited to this example.

The controlling device 5 is configured to process the captured image signal input thereto from the camera head 9 via the transfer cable 8, to output an image signal to the display device 4, and to control operations of the camera head 9 and the display device 4 in an integrated manner. Detailed configurations of the controlling device 5 will be explained later.

Figure 2:
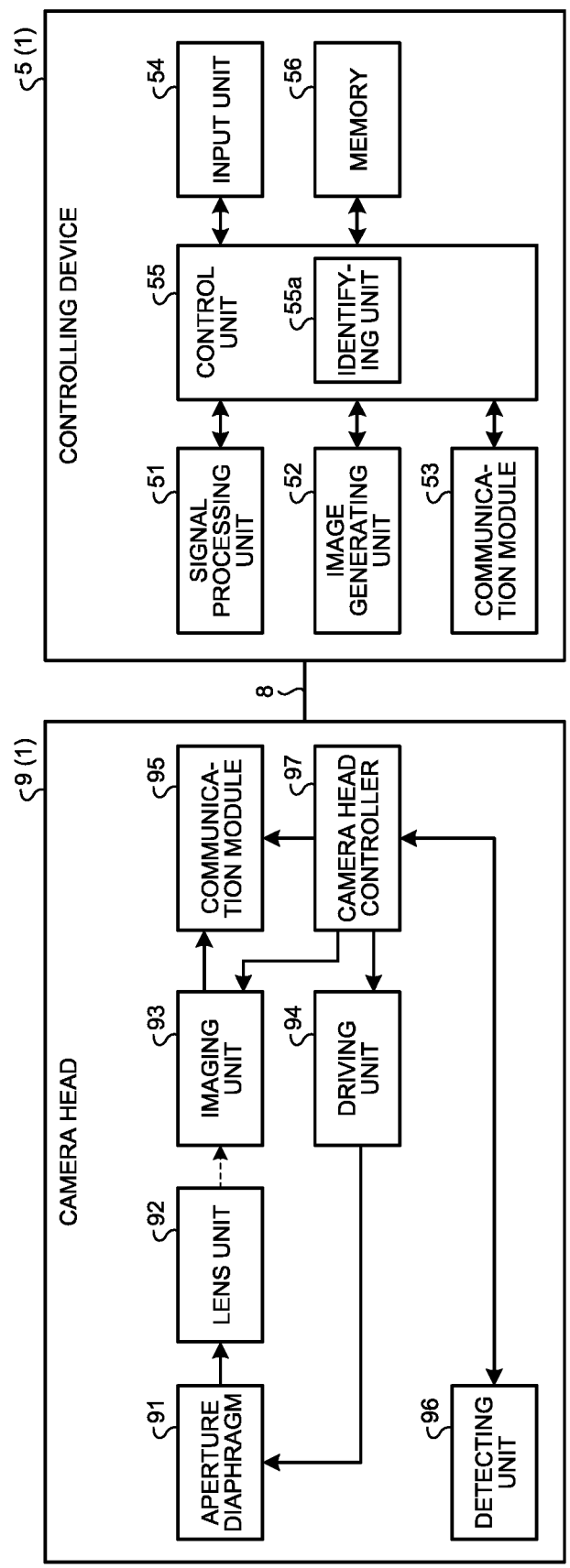
FIG. 2 is a block diagram illustrating configurations of the camera head and the controlling device illustrated in FIG. 1.

Next, configurations of the imaging device 3 and the controlling device 5 will be explained. FIG. 2 is a block diagram illustrating the configurations of the camera head 9 and the controlling device 5. In FIG. 2, the connector that makes the camera head 9 and the transfer cable 8 detachable from each other is omitted.

In the following sections, the configuration of the controlling device 5 and the configuration of the camera head 9 will sequentially be explained. In the present example, as the configuration of the controlling device 5, main parts will primarily be explained. As illustrated in FIG. 2, the controlling device 5 includes a signal processing unit 51, an image generating unit 52, a communication module 53, an input unit 54, a control unit 55, and a memory 56. The controlling device 5 may be provided with a power source unit (not illustrated) or the like configured to generate a power source voltage used for driving the controlling device 5 and the camera head 9, to supply the generated power source voltage to functional units of the controlling device 5, and to supply the same to the camera head 9 via the transfer cable 8.

The signal processing unit 51 is configured to output digitalized captured image signal (a pulse signal) to the image generating unit 52, by performing a noise elimination process and a signal processing process such as an A/D conversion, as necessary, on the captured image signal output from the camera head 9.

Further, the signal processing unit 51 is configured to generate the synchronization signal and the clock signal for the imaging device 3 and the controlling device 5. The synchronization signal (for example, a synchronization signal to instruct imaging timing of the camera head 9) and the clock signal (for example, a clock signal used for serial communication) for the imaging device 3 are sent to the imaging device 3 via a line (not illustrated), so that the imaging device 3 is driven on the basis of the synchronization signal and the clock signal.

On the basis of the captured image signal input thereto from the signal processing unit 51, the image generating unit 52 is configured to generate a display-purpose image signal to be displayed by the display device 4. By performing a predetermined signal processing process on the captured image signal, the image generating unit 52 generates the display-purpose image signal including the image of the imaged object. In this situation, as for the image processing process, the image generating unit 52 may perform any of publicly-known image processing processes such as various types of image processing processes including an interpolating process, a color correcting process, a color enhancing process, and a contour enhancing process, as well as a process of generating a captured image by increasing the depth of field through a restoring process performed on a signal of which the pupil function phase distribution has been modulated by a pupil modulation filter 21f (explained later). The image generating unit 52 performs the restoring process by performing a digital processing process that uses a point spread function (PSF). The image generating unit 52 outputs the generated image signal to the display device 4.

The communication module 53 is configured to output signals from the controlling device 5, which include a control signal (explained later) transmitted from the control unit 55, to the imaging device 3. Further, the communication module 53 is configured to output signals from the imaging device 3 to functional units in the controlling device 5. In other words, the communication module 53 is a relay device configured to output the signals from the functional units of the controlling device 5 to be output to the imaging device 3 by putting the signals together through a parallel-serial conversion or the like, for example, and to output the signals input thereto from the imaging device 3 to the functional units of the controlling device 5 by separating and distributing the signals through a serial-parallel conversion or the like, for example.

The input unit 54 is realized with a user interface such as a keyboard, a mouse, a touch panel, and/or the like and is configured to receive an input of various types of information.

The control unit 55 performs driving control on constituent elements including the controlling device 5 and the camera head 9 and input/output control of information to and from the constituent elements. The control unit 55 is configured to generate the control signal by referring to communication information data (e.g., communication-purpose format information) recorded in the memory 56 and to transmit the generated control signal to the imaging device 3 via the communication module 53. Further, the control unit 55 is configured to output the control signal to the camera head 9 via the transfer cable 8.

The control unit 55 includes an identifying unit 55a. The identifying unit 55a is configured to identify the type of the endoscope 2 connected to the camera head 9, on the basis of detection information output from the camera head 9.

The memory 56 is realized by using a semiconductor memory such as a flash memory, a dynamic random access memory (DRAM), or the like and has recorded therein the communication information data (e.g., the communication-purpose format information). Further, the memory 56 may also have recorded therein various types of computer programs executed by the control unit 55, or the like.

Further, the signal processing unit 51 may include: an AF processing unit that outputs a predetermined AF-specific evaluation value of each of the frames on the basis of captured image signals of the frames input thereto; and an AF calculating unit that performs an AF calculating process so as to select either a frame or a focus lens position or the like that is most suitable as a focal position on the basis of the AF-specific evaluation values of the frames output from the AF processing unit.

The signal processing unit 51, the image generating unit 52, the communication module 53, and the control unit 55 described above are realized by using a generic processor such as a central processing unit (CPU) or a dedicated processor represented by any of various types of computation circuits configured to execute specific functions such as an application specific integrated circuit (ASIC), the processor having an internal memory (not illustrated) that has a computer program recorded therein. Alternatively, those functional units may be configured by using a field programmable gate array (FPGA; not illustrated), which is a type of programmable integrated circuit. When those functional units are configured by using an FPGA, it is acceptable to provide a memory storing therein configuration data so as to configure the FPGA, which is a programmable integrated circuit, by using the configuration data read from the memory.

Next, as the configuration of the camera head 9, other main parts will primarily be explained. As illustrated in FIG. 2, the camera head 9 includes an aperture diaphragm 91, the lens unit 92, an imaging unit 93, a driving unit 94, a communication module 95, a camera head controller 97, and a detecting unit 96.

The aperture diaphragm 91 is arranged in such a position where the optical axis of the camera head 9 goes through and that is an incident pupil position of the lens unit 92. The aperture diaphragm 91 has formed therein an aperture through which the light condensed by the endoscope 2 passes. The aperture diaphragm 91 is configured with a shutter that is free to open and close and is configured so as to be able to change the diameter of the aperture under control of the driving unit 94. The present embodiment is explained by using an example in which the aperture diaphragm 91 is configured to electrically perform the aperture diameter changing operation under the control of the driving unit 94, as being triggered by pressing of a button (not illustrated) provided for the camera head 9, for example. However, another arrangement is also acceptable in which it is possible to mechanically change the diameter of the aperture by pressing a button or the like. The diameter of the aperture that may be arranged by the aperture diaphragm 91 will be explained later.

The lens unit 92 is structured by using one or more lenses and is configured to cause the image of the imaged object having passed through the aperture diaphragm 91 to be formed on an imaging surface of an imaging element structuring the imaging unit 93. The one or more lenses are each configured so as to be able to move along an optical axis. Further, the lens unit 92 is provided with an optical zoom mechanism (not illustrated) configured to vary the angle of view by moving the one or more lenses; and a focus mechanism configured to vary the focal point position. Further, besides the optical zoom mechanism and the focus mechanism, the lens unit 92 may be provided with an optical filter (e.g., a filter to eliminate infrared light) that is detachably inserted into a position on the optical axis, or the like.

The imaging unit 93 is configured to capture the image of the imaged object under control of the camera head controller 97. The imaging unit 93 is configured by using the imaging element that receives the image (light) of the imaged object formed by the lens unit 92 and to convert the received light into an electric signal. The imaging element may be configured by using a charge coupled device (CCD) image sensor or a complementary metal oxide semiconductor (CMOS) image sensor. When the imaging element is configured with a CCD, for example, a sensor chip has installed thereon a signal processing unit (not illustrated) configured to perform a signal processing process (e.g., an A/D conversion) on the electric signal (an analog signal) output from the imaging element and to output the captured image signal. When the imaging element is configured with a CMOS, for example, the imaging element includes a signal processing unit (not illustrated) configured to perform a signal processing process (e.g., an A/D conversion) on the electric signal (an analog signal) resulting from the conversion from the light to the electric signal and to output the captured image signal. The imaging unit 93 is configured to output the generated electric signal to the communication module 95.

The driving unit 94 includes a driver that is configured to bring the shutter of the aperture diaphragm 91 into operation so as to change the diameter of the aperture and is configured to bring the optical zoom mechanism and the focus mechanism into operation so as to change the angle of view and the focal point position of the lens unit 92, under control of the camera head controller 97.

The communication module 95 is configured to output the signal transmitted thereto from the controlling device 5 to functional units provided in the camera head 9 such as the camera head controller 97. Further, the communication module 95 is configured to convert information about the current state of the camera head 9 or the like into a signal format corresponding to a predetermined transfer scheme and to output the signal resulting from the conversion to the controlling device 5 via the transfer cable 8. In other words, the communication module 95 is a relay device configured to output the signals input thereto from the controlling device 5 and the transfer cable 8 to the functional units of the camera head 9 by separating and distributing the signals through a serial-parallel conversion or the like, for example, and to output the signals from the functional units of the camera head 9 to be output to the controlling device 5 and the transfer cable 8 by putting the signals together through a parallel-serial conversion or the like, for example.

The detecting unit 96 is configured to electrically detect positional arrangements of a plurality of pins that are provided in an endoscope 2A and an endoscope 2B, for example, while having mutually-different arrangement patterns. The detecting unit 96 is configured to electrically detect the arrangement patterns of the pins when an endoscope 2 is connected. The detecting unit 96 generates the detection information about the detected arrangement patterns of the pins. The detection information is used in the abovementioned process of identifying the endoscope 2 performed by the identifying unit 55a. Alternatively, the detecting unit 96 may be configured to generate the detection information by referring to, for example, information read from an IC tag or a barcode provided for the endoscope 2A and the endoscope 2B or information stored in a memory.

The camera head controller 97 is configured to control operations of the entirety of the camera head 9 in accordance with a drive signal input thereto via the transfer cable 8 and an instruction signal or the like output from an operating unit as a result of a user operation performed on the operating unit, which is, for example, a switch provided on the outer surface of the camera head 9 in an exposed manner. Further, the camera head controller 97 is configured to output the information about the current state of the camera head 9 to the controlling device 5 via the transfer cable 8.

The driving unit 94, the communication module 95, the camera head controller 97, and the detecting unit 96 described above are realized by using a generic processor such as a central processing unit (CPU) or a dedicated processor represented by any of various types of computation circuits configured to execute specific functions such as an ASIC, the processor having an internal memory (not illustrated) that has a computer program recorded therein. Alternatively, those functional units may be configured by using an FPGA, which is a type of programmable integrated circuit. When those functional units are configured by using an FPGA, it is acceptable to provide a memory storing therein configuration data so as to configure the FPGA, which is a programmable integrated circuit, by using the configuration data read from the memory.

It is also acceptable to configure the camera head 9 or the transfer cable 8 to have a signal processing unit configured to perform a signal processing process on the captured image signal generated by the communication module 95 and the imaging unit 93. Further, it is also acceptable to generate an imaging-purpose clock signal used for driving the imaging unit 93 and a driving-purpose clock signal used for driving the driving unit 94, on the basis of a reference clock signal generated by an oscillator (not illustrated) provided on the inside of the camera head 9 and to further output the generated clock signals to the imaging unit 93 and to the driving unit 94, respectively. It is also acceptable to generate timing signals for various types of processes performed by the imaging unit 93, the driving unit 94, and the camera head controller 97, on the basis of a synchronization signal input from the controlling device 5 via the transfer cable 8 and to further output the generated timing signals to the imaging unit 93, the driving unit 94, and the camera head controller 97, respectively. Alternatively, the camera head controller 97 may be provided for the transfer cable 8 or the controlling device 5, instead of for the camera head 9.

Figure 3A:
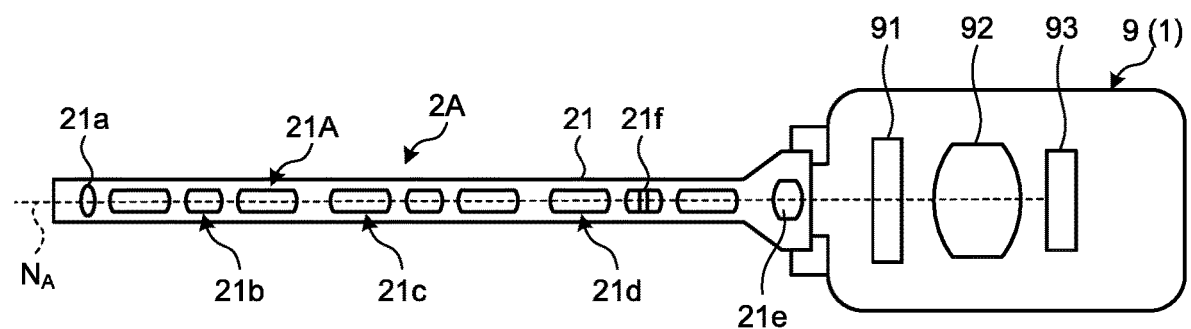
FIG. 3A is a schematic drawing for explaining configurations of an endoscope and the camera head according to the embodiment.
Figure 3B:
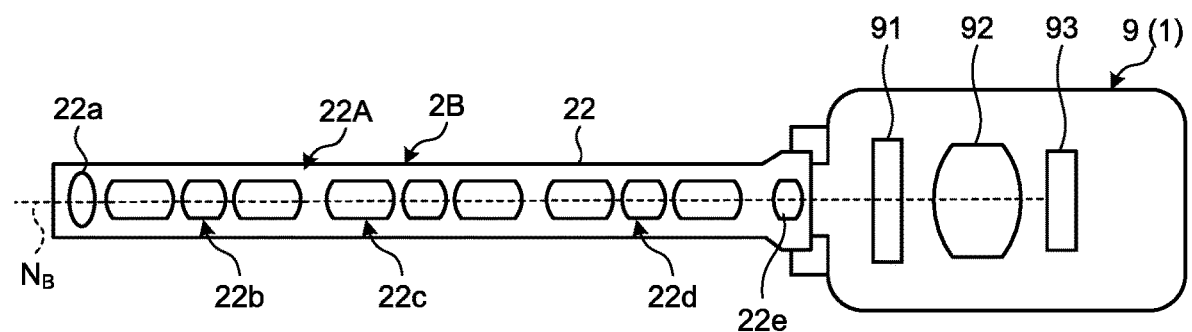
FIG. 3B is a schematic drawing for explaining configurations of another endoscope and the camera head according to the embodiment.

FIGS. 3A and 3B are schematic drawings for explaining configurations of the endoscope 2 and the camera head 9 according to the embodiment. Examples of the endoscope 2 that may be attached to the camera head 9 include the endoscopes 2A and 2B illustrated in FIGS. 3A and 3B. The endoscopes 2A and 2B are each configured to take in external light on the distal end side thereof and may each be connected to the camera head 9 on the proximal side thereof. The endoscopes 2A and 2B have mutually-different observation optical systems.

The endoscope 2A includes an observation optical system 21A provided on the inside of an insertion part 21. The observation optical system 21A is structured by positioning an objective lens 21a, a first relay optical system 21b, a second relay optical system 21c, a third relay optical system 21d, and an ocular lens 21e that are arranged along an optical axis NA of the observation optical system 21A from the distal end side in the stated order. Further, the third relay optical system 21d, which is positioned on the farthest proximal end side among the three relay optical systems, is provided with the pupil modulation filter 21f serving as a phase modulation element. The pupil modulation filter 21f is configured by using a phase plate and is configured to form an intermediate image that is arranged to be out of focus by changing the image forming characteristics of the observation optical system 21A. The intermediate image is an image that is not dependent on differences in the focal point position.

The diameter of an insertion part 22 of the endoscope 2B is larger than the diameter of the insertion part 21. The endoscope 2B includes an observation optical system 22A provided on the inside of the insertion part 22. The observation optical system 22A is structured by positioning an objective lens 22a, a first relay optical system 22b, a second relay optical system 22c, a third relay optical system 22d, and an ocular lens 22e that are arranged along an optical axis NB of the observation optical system 22A from the distal end side in the stated order. The maximum diameter observed along the optical axis NB direction in the observation optical system 22A is larger than the maximum diameter observed along the optical axis NA direction in the observation optical system 21A.

Further, the diameter rB of an exit pupil SB, which is equal to the dimension of the image of the imaged object formed by the observation optical system 22A included the endoscope 2B, is larger than the diameter rA of an exit pupil SA formed by the observation optical system 21A included in the endoscope 2A. In other words, the diameter rA of the exit pupil SA of the endoscope 2A is smaller than the diameter rB of the exit pupil SB of the endoscope 2B.

Figure 4A:
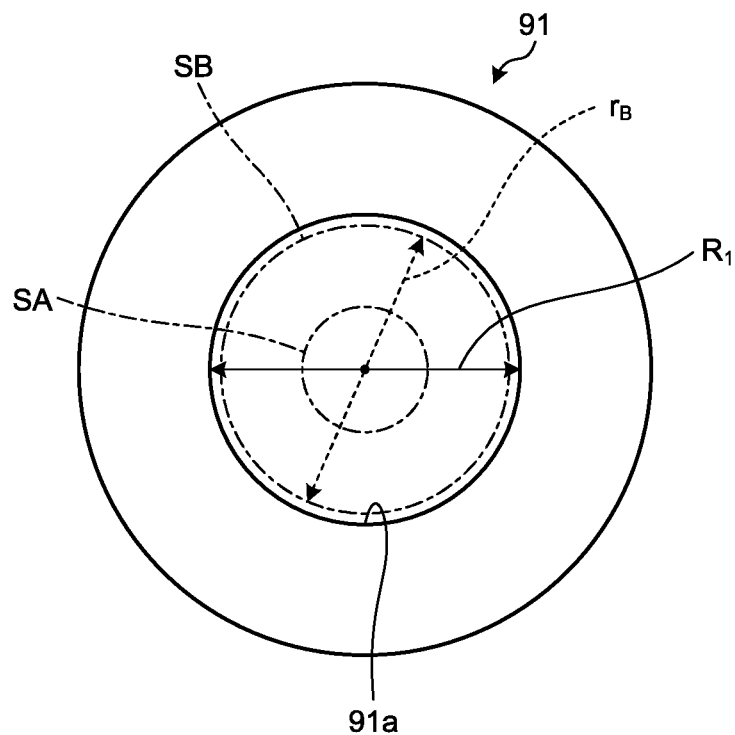
FIG. 4A is a drawing for explaining an aperture diameter of an aperture diaphragm according to the embodiment.
Figure 4B:
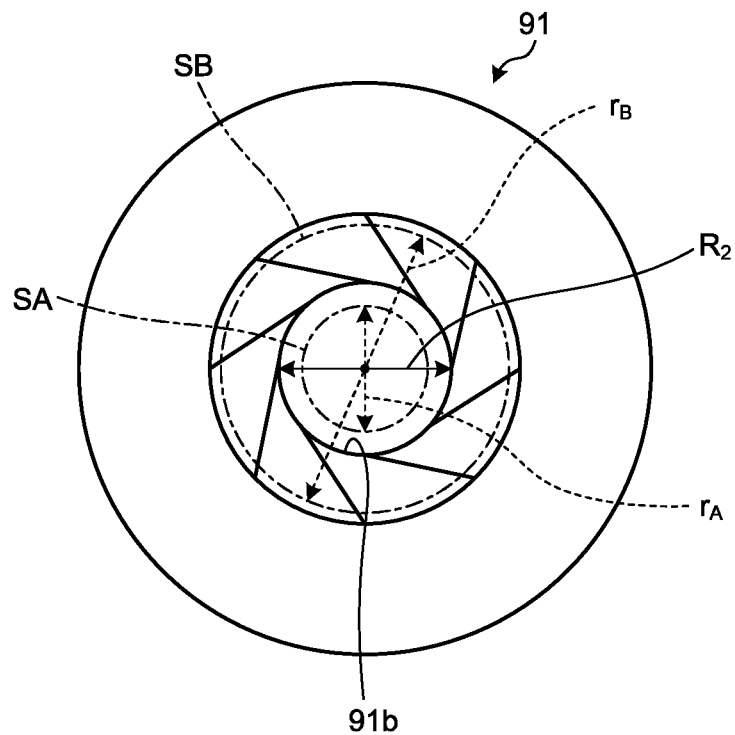
FIG. 4B is a drawing for explaining another aperture diameter of the aperture diaphragm according to the embodiment.

FIGS. 4A and 4B are drawings for explaining the aperture diameters of the aperture diaphragm 91 according to an embodiment. The aperture diaphragm 91 may be in either one of the two aperture patterns illustrated as a first aperture 91a (see FIG. 4A) and a second aperture 91b (see FIG. 4B) of which the diameter R2 is smaller than the diameter R1 of the first aperture 91a. The diameter R1 of the first aperture 91a is, for example, larger than the diameter rB of the exit pupil SB of the endoscope 2B. The diameter R2 of the second aperture 91b is smaller than the diameter rB of the exit pupil SB of the endoscope 2B and is larger than the diameter rA of the exit pupil SA of the endoscope 2A.

Further, in the controlling device 5, it is identified whether the endoscope 2 being connected is the endoscope 2A or the endoscope 2B, on the basis of the detection information generated by the detecting unit 96. More specifically, the identifying unit 55a is configured to identify the endoscope 2 being connected, on the basis of the arrangement pattern of the pins detected by the detecting unit 96.

In the controlling device 5, when the identifying unit 55a has identified the type of the endoscope 2 being connected, the control unit 55 causes the image generating unit 52 to perform an image processing process corresponding to the endoscope 2 being connected. More specifically, when the identifying unit 55a has identified that the endoscope 2A is being connected which has the pupil modulation filter 21f and of which the exit pupil diameter is smaller than that of the endoscope 2B, the control unit 55 causes the image generating unit 52 to perform an image generating process including the abovementioned restoring process. As a result, an image having an increased depth of field is generated.

In contrast, when the identifying unit 55a has identified that the endoscope 2B is being connected which does not have the pupil modulation filter 21f and of which the exit pupil diameter is larger than that of the endoscope 2A, the control unit 55 causes the image generating unit 52 to perform an image processing process other than the abovementioned restoring process. In that situation, when the aperture of the aperture diaphragm 91 is the first aperture 91a, an image prioritizing the resolution is generated. In contrast, when the aperture of the aperture diaphragm 91 is the second aperture 91b, an image prioritizing an increase in the depth of field is generated. This image has an increased depth of field compared to the situation using the first aperture 91a. By varying the diameter of the aperture of the aperture diaphragm 91 according to the user's operation, it is possible to generate an image prioritizing one selected from between the resolution and an increase in the depth of field.

The technique by which the pupil modulation filter 21f is arranged with the observation optical system 21A so that, when an image is generated on the basis of light that has passed through the pupil modulation filter 21f, the depth of field is increased by generating the image while using a point spread function (PSF) is generally called wavefront coding (WFC).

According to the embodiment described above, the camera head 9 is provided with the aperture diaphragm 91 configured to form the first aperture 91a and the second aperture 91b having a diameter that is smaller than the diameter rB of the exit pupil SB of the endoscope 2B and is larger than the diameter rA of the exit pupil SA of the endoscope 2A including the pupil modulation filter 21f. Accordingly, regardless of whether the endoscope 2A is connected or the endoscope 2B, which does not have the pupil modulation filter 21f, is connected, the controlling device 5 provided in the subsequent stage is able to generate an image having an increased depth of field.

Further, in the embodiment described above, because the endoscope 2A is provided with the pupil modulation filter 21f, it is possible to generate the image having the increased depth of field, without the need to narrow the light from the endoscope 2 having the smaller diameter. Further, even when the optical axis NA of the observation optical system 21A of the endoscope 2A and the center of the aperture of the aperture diaphragm 91 of the camera head 9 become out of alignment due to wobbling or the like occurring at the time of attaching the endoscope 2A and the camera head 9 to each other, it is possible to properly generate an image having an increased depth of field. As a result, according to the present embodiment, it is possible to generate the image having the increased depth of field, without lowering the resolution.

Further, in the embodiment described above, selectively providing the pupil modulation filter 21f in accordance with the diameter of the insertion part 21 of the endoscope 2 and the diameter of the exit pupil makes it possible to generate an image having an increased depth of field, while inhibiting the resolution from being degraded. For this reason, it is possible to generate an image having an increased depth of field, without the need to provide all the endoscopes 2 with a pupil modulation filter 21f. Accordingly, with respect to the endoscopes 2 that are usable, it is possible to reduce the costs of providing the pupil modulation filter 21f therefor.

In this situation, due to an impact of a chromatic aberration on the optical axis of the observation optical system, the focal point position at the time when infrared light is radiated is different from the focal point position at the time when white light is radiated. Due to this positional difference, a problem could arise where, when images are captured while the focal point position is being fixed, one of the generated images becomes out of focus. However, according to the present embodiment, by using the abovementioned WFC scheme, it is possible to increase the depth of field while including the difference in the focal point position. It is therefore possible to inhibit the image from becoming out of focus, even when the illumination light is changed while the focal point position is being fixed. In particular, when a superimposed image is generated by superimposing an infrared image using infrared light and a white image using white light on top of each other, it is possible to obtain a superimposed image that has a large depth of field and is clear.

In the embodiment described above, besides the endoscope 2A, when it is possible to attach, to the camera head 9, another endoscope 2 which has a pupil modulation filter and of which the exit pupil diameter is different, the diameter R2 of the second aperture 91b shall be arranged to be larger than the largest exit pupil diameter among the exit pupil diameters of all the endoscopes 2 each having a pupil modulation filter. In other words, the diameter R2 of the second aperture 91b is arranged to be smaller than the diameter R1 of the first aperture 91a and is larger than the largest exit pupil diameter among all the endoscopes 2 each having a pupil modulation filter.

In the embodiment described above, the example is explained in which, when the endoscope 2B is connected to the camera head 9, it is possible to select from between an image prioritizing the resolution and an image prioritizing an increase in the depth of field in accordance with the aperture of the aperture diaphragm 91; however, when only an image prioritizing an increase in the depth of field is to be generated, the aperture of the aperture diaphragm 91 may be fixed with the second aperture 91b. In other words, when the endoscope apparatus 1 is configured to only generate an image prioritizing an increase in the depth of field, the aperture diaphragm 91 has the shape of a hollow disc fixed with the second aperture 91b.

Further, in the embodiment described above, besides the endoscope 2B, when it is possible to attach an endoscope 2 having no pupil modulation filter and having a different exit pupil diameter to the camera head 9, the diameter R1 of the first aperture 91a of the aperture diaphragm 91 may be variable. In other words, for the diameter R1 of the first aperture 91a, an upper limit value is set to a diameter that is larger than the largest exit pupil diameter among the exit pupil diameters of such endoscopes 2 that have no pupil modulation filter, and a lower limit value is set to a diameter that is smaller than the smaller exit pupil diameter among the exit pupil diameters of such endoscopes 2 that have no pupil modulation filter. Further, the diameter R1 of the first aperture 91a of the aperture diaphragm 91 is arranged to be variable, so that it is possible to adjust the aperture diameter of the aperture diaphragm in accordance with the endoscope 2 being connected.

In the embodiment described above, when the endoscope 2A has no pupil modulation filter, the depth may be increased by performing an image processing process. In that situation, instead of performing the signal processing process using the Point Spread Function (PSF) on the captured image signal, the image generating unit 52 may generate a captured image having an increased depth of field by performing a contour enhancement process, for example. More specifically, when the endoscope 2A having no pupil modulation filter is connected, the image generating unit 52 performs an image processing process having a higher degree of enhancement in the contour enhancement process than that used when the endoscope 2B is connected, so as to increase the depth of field by expanding the area having a clear contour in the captured image. In this situation, it is also acceptable to arrange parameter settings for the contour enhancement process to be variable so that, for example, the degree of enhancement in the contour enhancement process is varied depending on regions within the captured image in accordance with Modulation Transfer Function (MTF) characteristics of the endoscope 2A being connected. In that situation also, it is possible to achieve the same advantageous effects as those in the embodiment described above.

In the embodiment described above, the example is explained in which, depending on the type of the endoscope 2 being connected, the depth of field is increased by applying the aperture diaphragm and the wavefront coding or applying the aperture diaphragm and the contour enhancement process; however, possible embodiments are not limited to this example. It is also acceptable to increase the depth of field by applying the wavefront coding and the contour enhancement process, without providing the aperture diaphragm 91. More specifically, regardless of the dimension of the exit pupil diameter of the endoscope 2, when an endoscope 2 having a pupil modulation filter is connected to the camera head 9, the image generating unit 52 may generate a captured image having an increased depth of field by performing a signal processing process that uses the point spread function (PSF) on the captured image signal, whereas when an endoscope 2 having no pupil modulation filter is connected to the camera head 9, the image generating unit 52 may generate a captured image having an increased depth of field by performing the contour enhancement process on the captured image signal. With these arrangements also, it is possible to generate an image having an increased depth of field in accordance with the endoscope 2 being connected. In those situations, it is also acceptable to vary the degree of enhancement in the contour enhancement process depending on the dimension of the exit pupil diameter of the endoscope 2 having no pupil modulation filter. For example, the smaller the exit pupil diameter of the endoscope 2 is, the relatively higher the degree of enhancement may be arranged to be.

In the embodiment described above, when the depth of field is increased by applying the aperture diaphragm and/or the wavefront coding, it is also acceptable to further increase the depth of field by additionally applying the contour enhancement process. In that situation, when an endoscope 2 to which the aperture diaphragm and/or the wavefront coding are inapplicable is connected to the camera head 9, the increase in the depth field is realized by making the degree of enhancement in the contour enhancement process higher than that used when an endoscope 2 to which the aperture diaphragm and/or the wavefront coding are applicable is connected to the camera head 9. In this situation also, it is possible to achieve the same advantageous effects as those in the embodiment described above.

Some of the embodiments to carry out the present disclosure have thus been explained; however, the present disclosure is not limited to the embodiments described above. Although the controlling device 5 is configured to perform the signal processing processes and the like in the embodiments described above, those processes may be performed on the camera head 9 side.

Further, the embodiments described above are based on the premise that the imaging device 3 connected to the controlling device 5 has installed therein a large-pixel-number imaging element of which the number of pixels is relatively large and requires an increase in the depth of field. However, possible embodiments are not limited to this example. For instance, it is also possible to selectively connect an imaging device (not illustrated) that does not require an increase in the depth of field because of, for example, having installed therein an imaging element of which the number of pixels is relatively small. In that situation, it is also acceptable to have an arrangement to selectively switch between the application and the non-application of the aperture diaphragm, the wavefront coding, and/or the contour enhancement process used for the purpose of increasing the depth of field, in correspondence with the situation where the imaging device 3 is connected to the controlling device 5 and with the situation where an imaging device having installed therein an imaging element of which the number of pixels is relatively small is connected to the controlling device 5. Further, another arrangement is also acceptable in which, depending of the type of the endoscope 2 being connected, at least two selected from among the aperture diaphragm, the wavefront coding, and the contour enhancement process are applied in combination for the purpose of increasing the depth of field.

As explained above, the endoscope apparatus according to at least one aspect is useful for generating an image having an increased depth of field, regardless of the type of the endoscope being connected.

According to at least one aspect of the present disclosure, an advantageous effect is achieved where it is possible to generate an image having an increased depth of field, regardless of the type of the endoscope being connected.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An endoscope apparatus comprising:
   a first endoscope that includes a first observation optical system;
   a second endoscope that includes a second observation optical system different from the first observation optical system, an exit pupil diameter of the second endoscope being larger than an exit pupil diameter of the first endoscope;
   an imaging device that is connected to one of the first and the second endoscopes, and includes
   an aperture diaphragm configured to pass light output from the connected one of the first and the second endoscopes, and
   an imager configured to receive the light passed through the aperture diaphragm and convert the received light into an electric signal; and
   an image processing device configured to generate an image by using the electric signal generated by the imaging device, wherein
   the image processing device includes an identifying circuit configured to identify the endoscope connected to the imaging device, and the image processing device controls a diameter of the aperture diaphragm to be larger than the exit pupil diameter of the first endoscope based on a result of the identifying circuit.

2. The endoscope apparatus according to claim 1, wherein
   the first observation optical system includes a phase modulation element, and
   when the first endoscope is connected to the imaging device, the image processing device generates the image by performing an image processing process that uses a point spread function.

3. The endoscope apparatus according to claim 2, wherein
   the image processing device includes an identifying unit configured to identify the endoscope connected to the imaging device, and
   when the identifying unit identifies that the endoscope connected to the imaging device is the first endoscope, the image processing device generates the image by performing the image processing process that uses the point spread function.

4. The endoscope apparatus according to claim 1, wherein when the first endoscope is connected to the imaging device, the image processing device generates the image by making a degree of enhancement in a contour enhancement process higher than that used when the second endoscope is connected to the imaging device.

5. The endoscope apparatus according to claim 4, wherein
   the image processing device includes an identifying unit configured to identify the endoscope connected to the imaging device, and
   when the identifying unit identifies that the endoscope connected to the imaging device is the first endoscope, the image processing device generates the image by making a degree of enhancement in a contour enhancement process higher than that used when the second endoscope is connected to the imaging device.

6. The endoscope apparatus according to claim 1, wherein the image processing device controls a diameter of the aperture diaphragm based on whether or not the endoscope connected to the imaging device includes a pupil modulation filter, based on a result of the identifying circuit.

7. An endoscope apparatus comprising:
   an imaging device configured to connect to one of a first endoscope and a second endoscope, the first endoscope includes a first observation optical system, the second endoscope includes a second observation optical system different from the first observation optical system, and an exit pupil diameter of the second endoscope is larger than an exit pupil diameter of the first endoscope; and
   the imaging device includes
   an aperture diaphragm configured to pass light output from the connected one of the first and the second endoscopes, and
   an imager configured to receive the light passed through the aperture diaphragm and convert the received light into an electric signal, and
   an image processing device configured to generate an image by using the electric signal generated by the imaging device, wherein
   the image processing device includes an identifying circuit configured to identify the endoscope connected to the imaging device, and the image processing device controls a diameter of the aperture diaphragm to be larger than the exit pupil diameter of the first endoscope based on a result of the identifying circuit.

* * * * *